(12) United States Patent
Baumann et al.

(10) Patent No.: US 8,309,759 B2
(45) Date of Patent: Nov. 13, 2012

(54) PREPARING ETHER CARBOXYLATES

(75) Inventors: Robert Baumann, Mannheim (DE);
Markus Christian Biel, Mannheim (DE); Andreas Deckers, Flomborn (DE); Alfred Oftring, Bad Dürkheim (DE); Frank Rittig, Worms (DE); Wolfgang Staffel, Otterstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/029,676

(22) Filed: Feb. 17, 2011

(65) Prior Publication Data

US 2011/0207651 A1 Aug. 25, 2011

Related U.S. Application Data

(60) Provisional application No. 61/305,971, filed on Feb. 19, 2010.

(51) Int. Cl.
*C07C 51/295* (2006.01)
*C07C 51/235* (2006.01)
*C07C 227/02* (2006.01)
*C11D 3/37* (2006.01)

(52) U.S. Cl. ........ 562/400; 562/583; 562/587; 560/180; 510/477; 510/488

(58) Field of Classification Search ................. 510/477, 510/488; 560/180; 562/400, 583, 587
See application file for complete search history.

(56) References Cited

U.S. PATENT DOCUMENTS

| 2,183,853 A | 12/1939 | Haussmann et al. |
| 2,384,817 A | 9/1945 | Chitwood |
| 2,384,818 A | 9/1945 | Curme, Jr. et al. |
| 3,717,676 A | 2/1973 | Bechara et al. |
| 3,799,977 A | 3/1974 | Rutledge |
| 3,935,257 A | 1/1976 | Ruest et al. |
| 4,110,371 A | 8/1978 | Schulze et al. |
| 5,916,840 A | 6/1999 | Ebner et al. |
| 6,159,894 A | 12/2000 | Eisenhuth et al. |
| 6,239,312 B1 | 5/2001 | Villanti et al. |
| 6,294,693 B1 * | 9/2001 | Asakawa et al. .............. 562/583 |
| 2003/0097020 A1 | 5/2003 | Franczyk, II et al. |

FOREIGN PATENT DOCUMENTS

| DE | 3135946 A1 | 3/1983 |
| EP | 0 620 209 A1 | 10/1994 |
| EP | 0 945 428 A2 | 9/1999 |
| EP | 1 125 633 A2 | 8/2001 |
| EP | 1 125 634 A1 | 8/2001 |
| EP | 1 382 390 A1 | 1/2004 |
| JP | 10-277391 | 10/1998 |
| WO | WO 96/01146 | 1/1996 |
| WO | WO 98/13140 | 4/1998 |
| WO | WO 03/033140 A2 | 4/2003 |
| WO | WO 2008/071582 A1 | 6/2008 |

OTHER PUBLICATIONS

International Search Report issued Aug. 10, 2011, in PCT/EP2011/051993 (with English Translation of Category of Cited Documents).
U.S. Appl. No. 13/030,816, filed Feb. 18, 2011, Baumann, et al.

* cited by examiner

*Primary Examiner* — Brian P Mruk
(74) *Attorney, Agent, or Firm* — Oblon, Spivak, McClelland, Maier & Neustadt, L.L.P.

(57) ABSTRACT

The present invention relates to a process for preparing ether carboxylates.

17 Claims, No Drawings

PREPARING ETHER CARBOXYLATES

The instant application claims benefit of Provisional Ser. No. 61/305,971, filed on Feb. 19, 2010.

The present invention relates to a process for preparing ether carboxylates. Ether carboxylates are typically prepared in a batch operation, normally by initially charging the alkxoylate, a base such as NaOH and a catalyst such as Raney copper and bringing this reaction mixture to reaction temperature under superatmospheric pressure.

The class of ether carboxylates, useful as mild anionic surfactants, is long known. U.S. Pat. No. 2,183,853, having a 1934 priority date, describes preparing ether carboxylates by reacting alkoxylates with sodium and sodium chloroacetate at temperatures between 160 and 200° C. To achieve high conversions and low by-product formation, it is described as advantageous to add the base and chloroacetic acid at different points of the reactor with stirring. To remove resulting or added water from the reaction solution and to achieve a very quick reaction, the reaction is carried out at 70 to 90° C. and a pressure of about 10 to 50 mbar.

DE 31 35 946 describes the direct oxidation of the alkoxylates with oxygen or oxygen-containing gases in an aqueous alkali medium over a platinum or palladium catalyst as a further way of preparing ether carboxylates.

The oxidative dehydrogenation of alcohols to carboxylates by thermal reaction of the alcohol with alkali metals or alkali metal hydroxides has been known since 1840 (Dumas and Stag, Ann, 35, 129 to 173). This reaction was classically carried out without catalyst and at >200° C. U.S. Pat. No. 2,384,818, issued 1945, employs this method for oxidizing amino alcohols.

Similarly, the use of catalysts for the oxidative dehydrogenation is long known. U.S. Pat. No. 2,384,817, filed 1942, describes the positive influence of cadmium, copper, nickel, silver, lead and zinc compounds on the reaction rate.

EP 0 620 209 describes a process to manufacture carboxylic acid salts by contacting an aqueous solution of a primary alcohol with an alkali metal hydroxide in the presence of an effective amount of a specific and activated Raney copper catalyst containing from 50 to 10,000 ppm of an element selected from the group consisting of chromium, titanium, niobium, tantalum, zirconium, vanadium, molybdenum, manganese, tungsten, cobalt and mixtures thereof, or from 50 to 10,000 ppm of nickel. The alcohol may be aliphatic, aromatic or a polyol. It is stated that both the alcohol—which necessarily will have a certain solubility in water—and the resulting carboxylate have to be stable in the hot and caustic solution. In addition, superatmospheric pressure is necessary for the reaction in order that the reaction temperatures described may be attained. Amino alcohols, aromatic alcohols and ethylene glycol are recited as examples.

EP 1 125 633 describes the use of doped Raney copper (doped with at least one element from the iron group or with a precious metal), the inactivation of which by agglomeration is distinctly reduced and the use cycles are therefore higher. The invention relates to the preparation of carboxylic acids from alcohols. Again, the oxidative dehydrogenation of diethanolamine under strongly basic conditions at 160° C. and 10 bar pressure is given as an example. The alcohols have to be soluble in water and the alcohol and also the carboxylic acid have to be stable to the strongly basic solution.

EP 1 125 634 describes a Raney copper fixed bed catalyst (with doping from iron or a precious metal), its simple filterability from the reaction solution and its use in the context of a continuous process. It is stated to be a prerequisite for the reaction of the alcohols that both the reactant and the product have to be stable in the strongly basic solutions and the alcohol has to be soluble in water.

U.S. Pat. No. 5,916,840 describes preparing carboxylic acid salts in the presence of a supported catalyst consisting of an alkali-resistant support material (activated carbon for example), an anchor metal (palladium for example) and a discretely applied active metal (copper for example). The reaction takes place in a batch autoclave in the presence of water at 160 to 170° C. Continuing this principle, WO 03/033140 describes further catalysts for preparing iminodiacetic acid from diethanolamine. The preferred reaction condition is said to be the use of alkali metal hydroxides (equimolar use), use of a solvent and of a catalyst (at least 1% by mass) at temperatures of 120 to 220° C. under superatmospheric pressure.

WO 98/13140 describes a catalyst for dehydrogenation of amino alcohols and ethylene glycol derivatives, consisting of zirconium, copper and optionally a further metal. The reaction of ethylene glycols such as triethylene glycol with 1 eq of NaOH in aqueous solution at 180° C. and 10 bar pressure over the described catalyst (30% by mass) is disclosed.

U.S. Pat. No. 4,110,371 describes a process for preparing dicarboxylic acid salts from compounds consisting of 2 to 6 ethylene glycol units with aqueous alkali metal hydroxide solution at temperatures of 200 to 300° C. using a catalyst consisting of nickel, copper and chromium.

U.S. Pat. No. 3,717,676 describes a method of preparing alkali metal salts of oxypolycarboxylates wherein an oxysubstituted or polyoxysubstituted primary alcohol is reacted with alkali metal hydroxide, 20% to 60% of water at 190 to 230° C., a pressure of 7 to 14 bar over a cadmium catalyst.

JP 10 277 391 finally describes the use of ultra-fine copper catalysts having particle sizes of 1 to 20 microns for preparing alkyl ether carboxylates from polyoxyethylene alkyl ethers and their use as an anionic surfactant in soap and cosmetic applications. The fine state of subdivision of the catalyst gives a distinctly higher activity than classic Raney copper or copper-zirconium catalysts (comparative example involving Raney copper from Degussa shows a conversion of merely 15% instead of 98% under otherwise equivalent conditions).

The processes described accordingly all have a number of disadvantages which it has proved impossible to overcome despite the many years of research in this field. A combination of pressure, high temperatures and strongly alkaline conditions is as ever required, imposing a severe stress on the material used (stress corrosion cracking), limiting reactivity as well as selectivity, the catalysts used are costly since they have to be inconveniently doped and form clumps during the process; only water-soluble and hence frequently rather short-chain alcohols can be used; moreover, the alcohol used and the product formed have to be base-resistant; and vinyl ethers, frequently formed as scissioning products, are not wanted in the product formed, yet are very difficult to detect analytically.

It is an object of the present invention to provide a process that reduces and/or eliminates the disadvantages mentioned.

We have found that this object is achieved, surprisingly, by a process for preparing an ether carboxylate of formula I

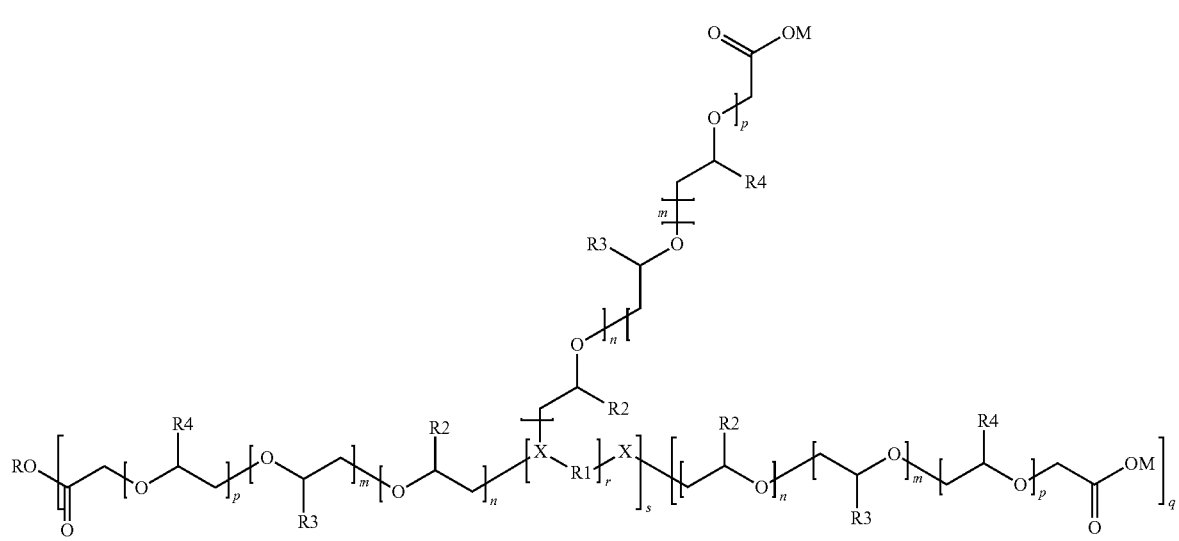

comprising reacting the corresponding alkoxylate of formula II

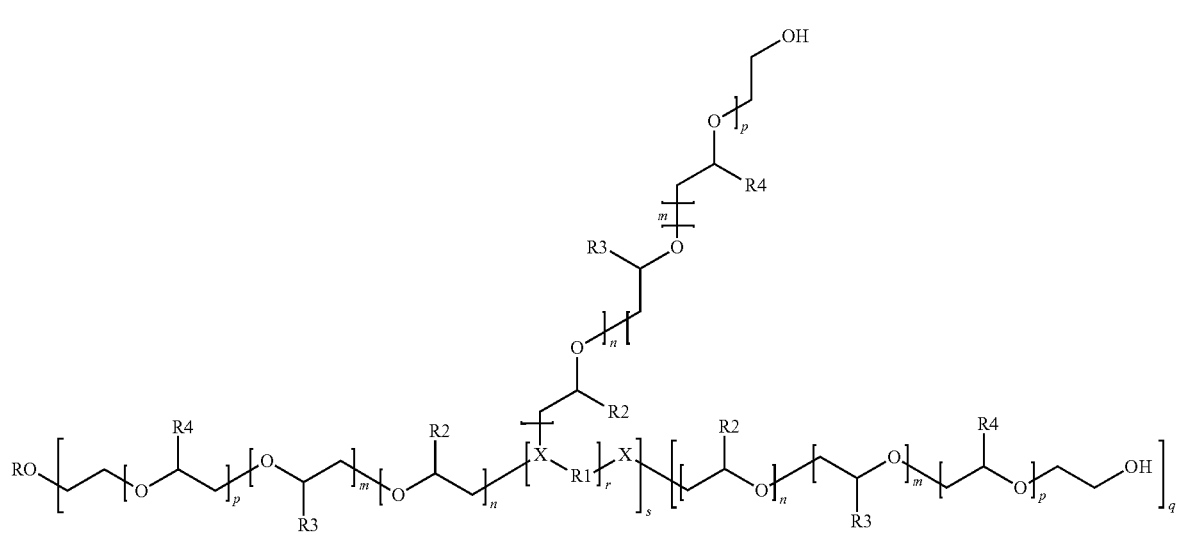

where independently
R1 is a $C_1$- to $C_{50}$-alkyl, mono-, di-, tri-, . . . polyamine,
X is O, COO, $CH_2$—NH—O for r=0 and q=1 or N,

$N(CH_2)_tO$ for r=0 to 50 and q=2,
r is an integer from 0 to 50,
R2 is H or $C_1$- to $C_{10}$-alkyl,
R3 is H or $C_1$- to $C_{10}$-alkyl,
R4 is H or $C_1$- to $C_{10}$-alkyl,
M is H or a metal, preferably alkali, alkaline earth, ammonium, organic base,
n is from 0 to 50,
m is from 0 to 40,
p is from 0 to 40,
q is from 1 to 20,
s is 0 or 1,
t is from 0 to 20,
provided that n+m+p is at least 1 and
R is $C_1$- to $C_{50}$-alkyl, $C_1$- to $C_{50}$-alkenyl, $C_1$- to $C_{50}$-alkynyl, $C_6$- to $C_{50}$-aryl, $C_6$- to $C_{50}$-alkylaryl, H or a metal, preferably alkali, alkaline earth,
with a base by using a transition metal catalyst, the base being added to the reaction mixture discontinuously at two or more times or continuously over a period above 30 minutes.

There are various preferred embodiments; in one, when s is 0, R is $C_1$- to $C_{50}$-alkyl, $C_1$- to $C_{50}$-alkenyl, $C_1$- to $C_{50}$-alkynyl, $C_6$- to $C_{50}$-aryl or $C_6$- to $C_{50}$-alkylaryl; in the other, when s is 1, R is H or a metal, preferably alkali, alkaline earth.

There are also preferred ranges for r. r is preferably from 1 to 20 and more preferably from 2 to 10.

Preference is given to a process for preparing an ether carboxylate of formula III

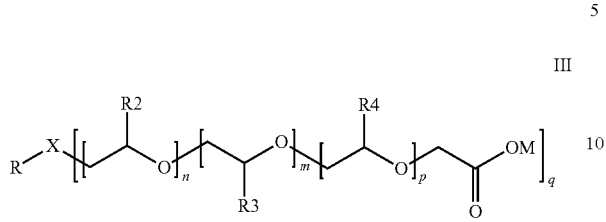

comprising reacting the corresponding alkoxylate of formula IV

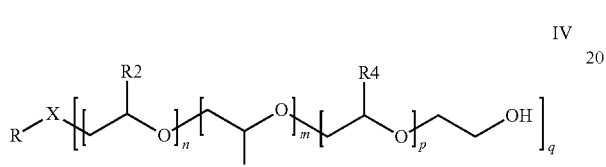

where independently

R is $C_1$- to $C_{50}$-alkyl, $C_1$- to $C_{10}$-alkenyl, $C_1$- to $C_{10}$-alkynyl, $C_6$- to $C_{50}$-aryl, $C_6$- to $C_{50}$-alkylaryl, H or a metal, preferably alkali, alkaline earth, X is O, COO, $CH_2$—NH—O for q=1 or N,

$N(CH_2)_tO$ for q=2

R2 is H or $C_1$- to $C_{10}$-alkyl,
R3 is H or $C_1$- to $C_{10}$-alkyl,
R4 is H or $C_1$- to $C_{10}$-alkyl,
M is H or a metal, preferably alkali, alkaline earth, ammonium, organic base,
n is from 0 to 50,
m is from 0 to 40,
p is from 0 to 40,
q is from 1 to 2,
t is from 1 to 10,
provided that n+m+p is at least 1,
with a base by using a transition metal catalyst, the base being added to the reaction mixture discontinuously at two or more times or continuously over a period above 30 minutes.

A process for preparing an ether carboxylate of formula V

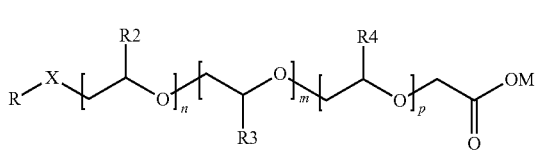

comprising reacting the corresponding alkoxylate of formula VI

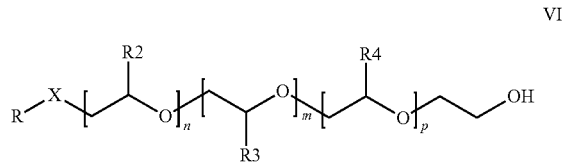

where independently R is $C_1$- to $C_{10}$-alkyl, $C_1$- to $C_{10}$-alkenyl, $C_1$- to $C_{10}$-alkynyl, $C_6$- to $C_{50}$-aryl, $C_6$- to $C_{50}$-alkylaryl, H or a metal, preferably alkali, alkaline earth, X is O,
R2 is H or $C_1$- to $C_{10}$-alkyl,
R3 is H or $C_1$- to $C_{10}$-alkyl,
R4 is H or $C_1$- to $C_{10}$-alkyl,
n is from 0 to 50,
m is from 0 to 40,
p is from 0 to 40, preferably from 1 to 20 and more preferably from 5 to 10,
provided that n+m+p is at least 1,
with a base by using a transition metal catalyst, the base being added to the reaction mixture discontinuously at two or more times or continuously over a period above 30 minutes.

There are preferred versions with regard to the alkoxylates used so that a process is preferred wherein independently R is $C_1$- to $C_{50}$-alkyl, $C_1$- to $C_{50}$-alkenyl, $C_1$- to $C_{50}$-alkynyl, $C_6$- to $C_{50}$-aryl, $C_6$- to $C_{50}$-alkylaryl, H or a metal, preferably alkali, alkaline earth, X is O,
R2 is H or $C_2$- to $C_8$-alkyl,
R3 is H or $C_2$- to $C_8$-alkyl,
R4 is H or $C_2$- to $C_8$-alkyl,
n is from 1 to 30,
m is from 1 to 20,
p is from 1 to 20,
n+m+p is at least 2.

Particular preference is given to a process wherein independently

X is O or COO,
R is $C_2$- to $C_{10}$-alkyl,
R2 is H or $C_3$- to $C_5$-alkyl,
R3 is H or $C_3$- to $C_8$-alkyl,
R4 is H or C3- to $C_8$-alkyl,
n is from 1 to 18,
m is from 1 to 12,
m is from 1 to 12,
n+m+p is at least 5.

R is more particularly methyl, ethyl, propyl, butyl, pentyl, hexyl, octyl, 2-ethylhexyl and 2-propylheptyl, dodecyl, tridecyl, myristyl, lauryl, i-C17, tall oil fat (C16,18), behenyl.

R2, R3 and R4, if present, are each more particularly and independently hydrogen, methyl, ethyl, propyl, butyl, pentyl and isobutyl, of which hydrogen, methyl and ethyl are particularly preferred and methyl and ethyl are very particularly preferred.

n is most preferably in the range from 3 to 20.
m is more preferably in the range from 3 to 20.
p is more preferably in the range from 3 to 20.

The sum total of n, m and p is more preferably in the range from 3 to 20. The individual alkoxide units can be arranged in various ways, for example randomly, in block form or with a gradient. Particular preference is given to processes first using a higher oxide, for example propylene oxide, and then EO.

In addition to various alkylene oxides, the process of the present invention may also utilize various alkoxylates a, b, c, z being added at one or more times. For instance, compounds where $Ra=C_{12,14}$ to $C_{20}$ and $Rb=C_2$ to $C_{10}$ may be used with advantage.

A useful base is in principle any compound capable of deprotonating the alkoxylate used. This includes bases within the meaning of Bjerrum's acid-base definition. There are certain preferred bases and hence a process wherein the base is selected from the group consisting of NaOH, KOH, $Mg(OH)_2$, Ca(OH)2, ammonium hydroxide, choline hydroxide and hydrotalcite constitutes a particularly preferred embodiment of the present invention. Hydrotalcite is particularly preferred when the product is to have narrow molar mass distributions.

The base is added to the reaction mixture during the reaction either batchwise or continuously. This means that the base, or portions of the base, are added to the reaction mixture at a time at which reaction conditions are present.

A preferred embodiment is accordingly a process wherein the base is added to the reaction mixture at 2 to 10,000 times. The number of times at which the base is added is preferably in the range from 3 to 1000, more preferably in the range from 4 to 100 and most preferably in the range from 5 to 20.

Another preferred embodiment is a process wherein the base is added to the reaction mixture over a period of more than 30 minutes. The period over which the base is added to the reaction mixture is particularly advantageous in the range from more than 2 h to 10 h, preferably in the range from 5 h to 9 h and even more preferably in the range from 6 h to 8 h.

In both cases, i.e., in the case of the continuous addition of the base and in the case of the batchwise addition of the base, the base can be introduced into the reaction mixture at various places. It is particularly preferable when the base is added to the reactor at 2 to 10 places and preferably at 3 to 5 places. This procedure can be used to reduce the local concentration of base in the reaction mixture still further and thereby further suppress the formation of by-products.

As far as the catalyst is concerned, the metals of groups 4 to 12, i.e., from Ti to Zn and those thereunder, come into consideration as both main and secondary constituent, those of groups 8 to 11, i.e., Fe—Cu and those thereunder, being preferred. And it is accordingly the case that a process wherein the transition metal catalyst comprises at least one metal selected from the group consisting of Fe, Cu, Co and Ni is preferred.

The transition metal can be in a variety of forms, such as pure metal or as metal oxide, but it is preferably present in activated form, as Raney metal. Raney copper is particularly preferred. This Raney copper can also be still further modified, for example by doping with other metals. It is an advantage of the process of the present invention that such doping is not needed to achieve a good result for the synthesis, but it may nevertheless be advantageous to further improve the result of the synthesis. The preparation of suitable transition metal catalysts is described for example in EP 1 125 634 (Degussa), where a simple Raney copper fixed bed catalyst is disclosed. EP 1 125 633 (Degussa) describes Raney copper comprising various dopants [example: 1% Pt, 3% Fe, 2000 ppm Cr or 1% V on Raney Cu], and it is shown that the doped catalysts deactivate less than conventional Raney copper (Degussa BFX 3113W). WO 96/01146 (Monsato) finally describes C support with a precious metal, for example Pt applied as anchor metal on the Cu. This technique is stated to likewise prevent the sintering of the Cu. A particularly preferred combination of transition metals is that of copper and iron. DMC catalysts are more particularly preferred.

The present process leaves only small amounts of catalyst in the product. In a preferred process the M content of the product is in the range from 0.1 ppm to 1%, preferably in the range from 1 to 500 ppm and more preferably in the range from 10 to 50 ppm.

The process of the present invention can pleasingly also be carried out on a large scale. Preference is accordingly given to a process utilizing more than 1 kg, preferably more than 10 kg, even more preferably more than 100 kg and most preferably more than 1 t (metric ton) of alkoxylate.

The process of the present invention wherein the reaction temperature is in the range from 140° C. to 220° C. is preferred. More preference is given to processes carried out in the temperature range from 160 to 200° C. and more particularly in the range from 160 to 190° C., for example at 180° C.

The process of the present invention may in principle employ any solvent that is stable under the reaction conditions and does not react with the reactants or with the products. Preference is therefore given to solvents selected from the following list:

| Name |
| --- |
| NMP |
| diethylene glycol dimethyl ether |
| triethylene glycol dimethyl ether |
| tetraethylene glycol dimethyl ether |
| diethylene glycol diethyl ether |
| [2-(2-methoxyethoxy)ethoxy] acid sodium salt |
| {2-[2-(2-methoxyethoxy)ethoxy]ethoxy}acetic acid |
| Decane |
| Decalin |
| Dodecane |
| white oil |
| 1,1,3,3-tetramethylurea |
| Tributylamine |
| γ-butyrolactone |
| Undecane |
| tert-butylbenzene |
| dipropyl carbonate |
| 2,5-dimethylpyrrole |
| 2,6-dimethylanisole |
| 3,4-dimethylanisole |
| 1,2-dimethylimidazole |
| 4-tert-butyl-1,2-dimethylbenzene |

And particular preference is given to the following solvents or suspension media: N-methylpyrrolidone, triethylene glycol dimethyl ether, [2-(2-methoxyethoxy)ethoxy] acid sodium salt and white oil.

There is also a preferred pressure range. Preference is given to a process wherein the pressure in the reaction vessel is less than 10 bar, preferably less than 5 bar and more preferably less than 2 bar. It is a particular advantage of the process of the present invention that it can also be carried out under atmospheric pressure, and that is in fact the most preferred embodiment.

Also protected are the ether carboxylates obtainable by this process and obtained by this process.

The use of these ether carboxylates in cleaning, crop protection and cosmetic applications and also as a solubilizer constitutes a further part of the subject matter of the present invention.

Compositions comprising ether carboxylates obtained by this process likewise form part of the subject matter of the present invention.

Further common constituents of compositions of this kind are mentioned in

The present invention is more particularly elucidated by the following examples, which do not restrict the scope of the invention:

EXAMPLES

Example 1

Synthesis of Nonionic Ethoxylate (Surfactant A)

300 g of a $C_{12,14}$ alcohol mixture of $C_8$<0.3% by weight, $C_{10}$<1.0% by weight, $C_{12}$>65.0% by weight, $C_{14}$ 21.0% to 28.0% by weight, $C_{16}$ 4.0% to 8.0% by weight, $C_{18}$<0.5% by weight, for example Radianol $C_{12}$-$C_{16}$ 1726 from Oleon, were initially charged with 2.6 g KOH (45% by weight in water) and dewatered together at 80° C. and reduced pressure (about 20 mbar). Next 462 g of ethylene oxide were added by metered addition at 150° C. and reacted at that temperature. The end of the reaction was determined via the drop in pressure. After purging with inert gas and cooling down to room temperature, the catalyst was neutralized by addition of 1.25 g of concentrated acetic acid.

Example 2

Oxidative Dehydrogenation under Atmospheric Pressure in Semi-Batch Process

A 2 l multi-neck flask equipped with internal thermometer, dropping funnel and distillation still head with column was initially charged with 498 g of surfactant A and also 30 g of Raney copper and the initial charge was heated to 180° C. with stirring. 152 g of aqueous sodium hydroxide solution (25% strength) were added dropwise over a period of 8 h during which the water was distilled out of the reaction mixture. On completion of the addition of the aqueous sodium hydroxide solution the reaction mixture was stirred for a further 30 minutes. The reaction mixture was cooled down to 140° C. and filtered through a frit and the effluent was analyzed.

Strong base titration:
7 mg KOH/g
Weak base titration:
95 mg KOH/g
OH number analysis:
reactant: 119 mg KOH/g effluent: 13 mg KOH/g, corrected with strong base: 6 mg KOH/g; it follows that the conversion was 95%.

NMR (DMSO, CDCI3=1/1); $^1$H NMR, $^{13}$C decoupled: δ=0.85 (t, 3H,—CH$_3$), 1.25 (s, 20H, CH$_2$), 1.55 (m, 2H, —CH$_2$CH$_2$—O), 3.4 (m, 2H, CH$_2$—O), 3.6 (m, 24H, O—CH$_2$—CH$_2$—O and CH$_2$—OH of reactant), 3.75 (s, 1.77H, CH$_2$—COO). It follows that the conversion was 89%.

HPLC: the sample was resolved in a system developed for the determination of free polyethylene glycol in nonionic surfactants. The principle of the analysis is that molecules having aliphatic moieties are retained on a reversed phase, whereas polar substances pass through the column without being retained. A switch valve was used to transfer the non-retarded fraction to a size exclusion column, on which the polymeric constituents were separated from low molecular weight secondary components. The level of scissioning products in the analyzed sample was below 0.5 g/100 g.

Example 3

Oxidative Dehydrogenation under Superatmospheric Pressure in Batch Process

A 1.2 l autoclave with pressure maintenance at 15 bar was initially charged with 249 g of surfactant A together with 15 g of Raney copper (Degussa) and 76 g of aqueous sodium hydroxide solution (25%) and this initial charge was heated to 180° C. for 10 h with stirring. After removal of the catalyst by filtration, the organic phase was separated and titrated for weak base (6 mg KOH/g) and subjected to an OH number measurement (113 mg KOH/g) to determine conversion (6%).

Example 4

Oxidative Dehydrogenation under Superatmospheric Pressure in Semi-Batch Process

A 1.2 l autoclave with pressure maintenance at 15 bar was initially charged with 249 g of surfactant A together with 15 g of Raney copper (Degussa) and this initial charge was heated to 180° C. with stirring. In the course of 7 h, altogether 76 g of aqueous sodium hydroxide solution (25%) were metered into the autoclave using an HPLC pump, followed by a further 30 minutes of stirring. After removal of the catalyst by filtration, the organic phase was separated and titrated for weak base (9 mg KOH/g) and subjected to an OH number measurement (115 mg KOH/g) to determine conversion (3.5%).

We claim:
1. A process for preparing an ether carboxylate of formula (I):

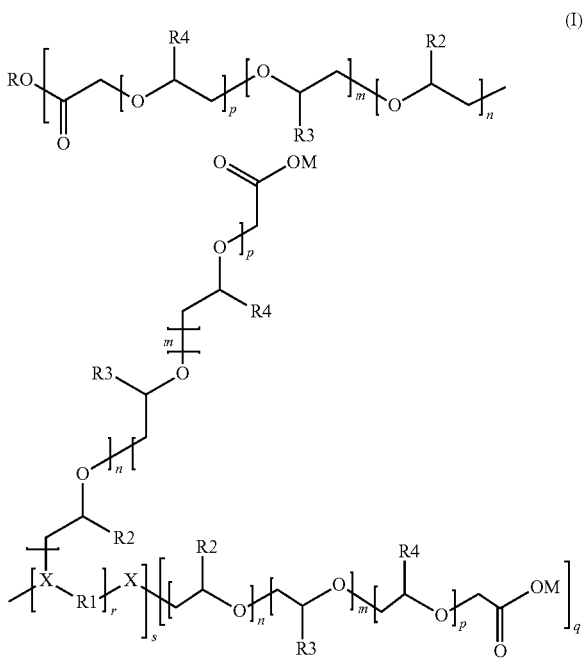

comprising reacting a corresponding alkoxylate of formula (II):

(II)

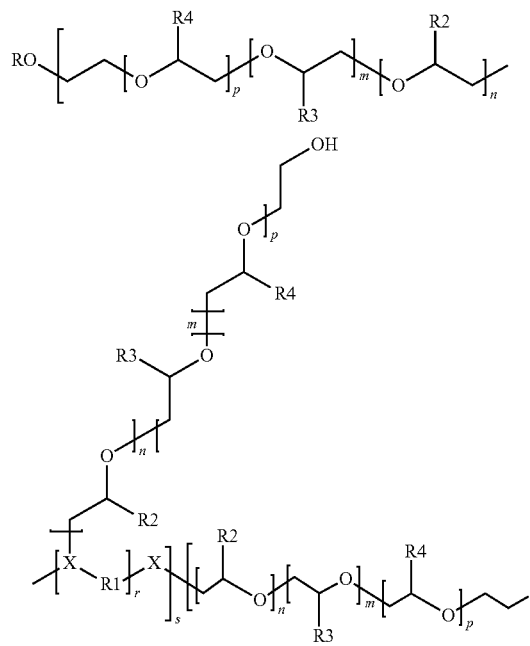

wherein

R1 is independently a $C_1$- to $C_{50}$-alkyl, mono-, di-, tri-, or higher polyamine, X is independently O, COO, $CH_2$—NH—O for q=1 and r=0 or N,

$N(CH_2)_t$ O for q=2 and r=0 to 50, r is independently an integer from 0 to 50, R2 is independently H or $C_1$- to $C_{10}$-alkyl, R3 is independently H or $C_1$- to $C_{10}$-alkyl, R4 is independently H or $C_1$- to $C_{10}$-alkyl, M is independently H or a metal, n is independently from 0 to 50, m is independently from 0 to 40, p is independently from 0 to 40, q is independently from 1 to 20, s is independently 0 or 1, t is independently from 0 to 20, provided that n+m+p is at least 1, and R is independently $C_1$- to $C_{50}$-alkyl, $C_1$- to $C_{50}$-alkenyl, $C_1$- to $C_{50}$-alkynyl, $C_6$- to $C_{50}$-aryl, $C_6$- to $C_{50}$-alkylaryl, H or a metal, with a base in the presence of a transition metal catalyst, such that the base is added to the reaction mixture discontinuously at two or more times or continuously over a period above 30 minutes.

2. A process for preparing an ether carboxylate of formula (III):

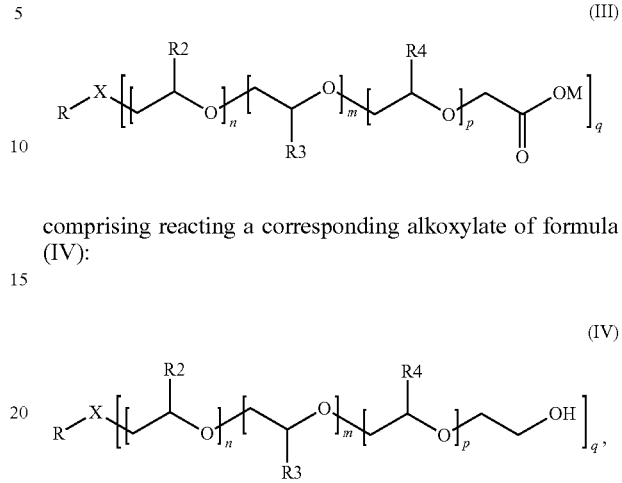

comprising reacting a corresponding alkoxylate of formula (IV):

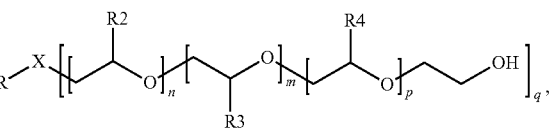

wherein where independently

R is independently $C_1$- to $C_{50}$-alkyl, $C_1$- to $C_{50}$-alkenyl, $C_1$- to $C_{50}$-alkynyl, $C_6$- to $C_{50}$-aryl, $C_6$- to $C_{50}$-alkylaryl, H or a metal, X is independently O, COO, $CH_2$—NH—O for q=1 or N,

$N(CH_2)_t$O for q=2,

R2 is independently H or $C_1$- to $C_{10}$-alkyl,

R3 is independently H or $C_1$- to $C_{10}$-alkyl,

R4 is independently H or $C_1$- to $C_{10}$-alkyl,

M is independently H or a metal, n is independently from 0 to 50, m is independently from 0 to 40, p is independently from 0 to 40, q is independently from 1 to 2, t is independently from 1 to 10, and provided that n+m+p is at least 1, with a base in the presence of a transition metal catalyst, such that the base is added to the reaction mixture discontinuously at two or more times or continuously over a period above 30 minutes.

3. A process for preparing an ether carboxylate of formula (V):

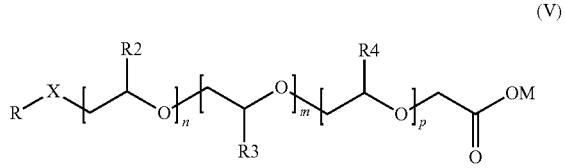

comprising reacting a corresponding alkoxylate of formula (VI):

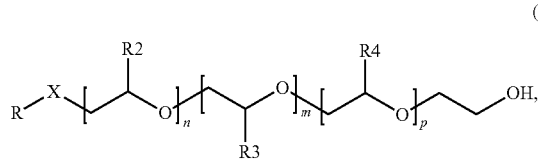

wherein
R is independently $C_1$- to $C_{50}$-alkyl, $C_1$- to $C_{50}$-alkenyl, $C_1$- to $C_{50}$-alkynyl, $C_6$- to $C_{50}$-aryl, $C_6$- to $C_{50}$-alkylaryl, H or a metal,
X is 0,
R2 is independently H or $C_1$- to $C_{10}$-alkyl,
R3 is independently H or $C_1$- to $C_{10}$-alkyl,
R4 is independently H or $C_1$- to $C_{10}$-alkyl,
M is independently H or a metal,
n is independently from 0 to 50,
m is independently from 0 to 40,
p is independently from 0 to 40, and
provided that n+m+p is at least 1,
with a base in the presence of a transition metal catalyst, such that the base is added to the reaction mixture discontinuously at two or more times or continuously over a period above 30 minutes.

4. The process according to claim 2 or 3 wherein independently
R is independently $C_1$- to $C_{50}$-alkyl, $C_1$- to $C_{50}$-alkenyl, $C_1$- to $C_{50}$-alkynyl, $C_6$- to $C_{50}$-aryl, $C_6$- to $C_{50}$-alkylaryl, H or a metal,
X is independently O,

COO, $CH_2$—NH—O, $N(CH_2)_tO$
R2 is independently H or $C_2$- to $C_8$-alkyl,
R3 is independently H or $C_2$- to $C_8$-alkyl,
R4 is independently H or $C_2$- to $C_8$-alkyl,
n is independently from 1 to 30,
m is independently from 1 to 20,
p is independently from 1 to 20,
n+m+p is at least 2, and
t is independently an integer from 1 to 10.

5. The process according to either of claims 2 and 3 wherein
X is independently O or COO,
R is independently $C_2$- to $C_{10}$-alkyl,
R2 is independently H or $C_3$- to $C_5$-alkyl,
R3 is independently H or $C_3$- to $C_5$-alkyl,
R4 is independently H or $C_3$- to $C_6$-alkyl,
n is independently from 1 to 18,
m is independently from 1 to 12,
m is independently from 1 to 12, and
n+m+p is at least 5.

6. The process according to claim 1, wherein the base is selected from the group consisting of NaOH, KOH, $Mg(OH)_2$, $Ca(OH)_2$, ammonium hydroxide, choline hydroxide and hydrotalcite.

7. The process according to claim 1, wherein the base is added to the reaction mixture at 2 to 10,000 times.

8. The process according to claim 1, wherein the base is added to the reaction mixture over a period of more than 30 minutes.

9. The process according to claim 1, claim wherein the transition metal catalyst comprises at least one metal selected from the group consisting of Fe, Cu, Co and Ni.

10. The process according to claim 1, wherein the reaction temperature is in the range from 140° C. to 220° C.

11. The process according to claim 1, wherein the pressure in the reaction vessel is less than 10 bar.

12. The process of claim 1, wherein M is independently an alkali metal, an alkaline earth metal, an ammonium or an organic base.

13. The process of claim 1, wherein R is independently an alkali metal or an alkaline earth metal.

14. The process of claim 2, wherein R is independently an alkali metal or an alkaline earth metal.

15. The process of claim 2, wherein M is independently an alkali metal, an alkaline earth metal, an ammonium or an organic base.

16. The process of claim 3, wherein R is independently an alkali metal or an alkaline earth metal.

17. The process of claim 3, wherein M is independently an alkali metal or an alkaline earth metal.

* * * * *